（12）United States Patent
Heinonen et al.

(10) Patent No.: US 7,699,789 B2
(45) Date of Patent: Apr. 20, 2010

(54) METHOD FOR MONITORING LUNG COLLAPSE

(75) Inventors: Erkki Heinonen, Helsinki (FI); Sören Söndergaard, Mölndal (SE)

(73) Assignee: The General Electric Company, Schenectady, NY (US)

( * ) Notice: Subject to any disclaimer, the term of this patent is extended or adjusted under 35 U.S.C. 154(b) by 819 days.

(21) Appl. No.: 11/231,625

(22) Filed: Sep. 21, 2005

(65) Prior Publication Data

US 2007/0062528 A1 Mar. 22, 2007

(51) Int. Cl.
*A61B 5/08* (2006.01)
(52) U.S. Cl. .................................. 600/538
(58) Field of Classification Search ............ 600/538; 128/204.21, 204.18, 204.23
See application file for complete search history.

(56) References Cited

U.S. PATENT DOCUMENTS 6,612,995 B2 * 9/2003 Leonhardt et al. .......... 600/532

OTHER PUBLICATIONS

Raoof et al., Effect of Combined Kinetic Therapy and Percussion Therapy on the Resolution of Atelectasis in Critically Ill Patients, Chest 1999;115;1658-1666.*
British Journal of Anesthesia 91 (1): 92-105 (2003); *Practical Assessment of Respiratory Mechanics*; Author, O. Stenqvist.
Anesthesiology, V. 79, No. 3, 503-513, Sep. 1993; *Continuous Calculation of Intratracheal Pressure in Tracheally Intubated Patients*; Authors, Josef Guttmann, Ph.D., Luc Eberhard, Eng., Ben Fabry, Eng., Wolfgang Bertschmann, M.D., Gunther Wolff, M.D.

* cited by examiner

*Primary Examiner*—Charles A Marmor, II
*Assistant Examiner*—Christian Y Jang
(74) *Attorney, Agent, or Firm*—Andrus, Sceales, Starke & Sawall, LLP

(57) ABSTRACT

A method for measuring lung collapse and for providing information regarding recruitment and successfulness of actions taken to recruit the lung is provided. Alveolar- and proximal pressures are determined at different lung pressures or volumes. Patient airway resistance is calculated combining these measurements with flow measurement. Plotting the resistance against the lung pressure or volume gives a within-breath distribution of the resistance. Increase of this resistance at end-expiration volume or pressure indicates lung collapse.

12 Claims, 3 Drawing Sheets

METHOD FOR MONITORING LUNG COLLAPSE

BACKGROUND

Improper ventilator settings during long-term ventilation may cause lung damage, known as ventilator induced lung injury (VILI). Limiting or eliminating VILI has been a topic of scientific discussion for years. As a result of this, two main damaging mechanisms have been identified: (1) shear stress caused by lung collapse at end-expiration and (2) over-distension causing tissue breakage allowing fluidic communication between alveolar space and lung capillaries.

To reduce VILI, lung-protective low tidal volume-high positive end-expiratory pressure (PEEP) ventilation strategies have been recommended. The high PEEP is used to prevent lung collapse. However, high PEEP distends the lung tissue, reducing the tidal volume range that can be used without overstretching the lungs. Therefore the strategy is accompanied with reduced tidal volume. Such strategies are also called permissive hypercapnia because low tidal volume may not maintain sufficient $CO_2$ clearance from the circulation, causing blood $CO_2$ content increase, i.e. hypercapnia. Hypercapnia is a non-normal physiological state in which negative side effects are possible. Therefore, optimal ventilation settings incorporate the lowest PEEP that prevents end-expiration collapse of the lungs to maximize the elastic lung volume range for the tidal volume.

Adjusting the ventilator for optimal PEEP for a particular patient is problematic since diagnostic real-time bedside measurements for lung collapse are missing. In state of the art therapy, common values based on statistical studies are used for patients classified to represent particular forms of lung sicknesses. From an individual patient point of view, such statistical values may be too low or too high compared to the optimal. Visual inspection for inflection point in the curvature of a graph where the breathing volume is presented as a function of breathing circuit pressure has been used. Locating this point is difficult and, when found, it may represent properties other than the end-expiratory lung collapse, such as properties of the chest wall, ventilator, breathing circuit, or endotracheal tube.

Although PEEP is very a common property of artificial ventilation and is effective in preventing lung collapse, it is not very effective in recruiting collapsed lung regions. For this purpose, recruitment manoeuvres are used wherein the lung is opened with one or more inspirations with increased tidal volume and duration. Also, patient positioning can be used to recruit the lungs. Prone or side positioning may open the lungs compared to more normal supine positions. Further forms of recruitment may be obtained by infusion of drugs, such as surfactants or bronchodilators. Clinical problems result however because direct measurements indicating the need for recruitment and its efficacy are missing at the bedside. Without such information, decisions have to be made based on indirect parameters such as oxygenation, which are not very sensitive for lung collapse.

SUMMARY OF INVENTION

This invention provides a method for measuring lung collapse and it provides information regarding the need for recruitment and successfulness of actions taken to recruit collapsed lung regions. These actions may include recruitment manoeuvres, adjustment of ventilator settings, change of patient position, drug delivery etc. Using the method of the invention, ventilation and patient position can be tailored to allow maximal elasticity range for tidal ventilation and $CO_2$ extraction. Ventilating at the lowest pressure level that prevents lung collapse maximizes the volume range that can be used for gas exchange without putting excessive tension on the lung tissue.

The method of the invention is based on measurement of the patient airway flow resistance. Patient airways are comprised of larger bronchi and a large number of smaller bronchioles ending up with alveoli. If the lung collapses towards the end of expiration, the number of airways carrying the flow is reduced. As well, reducing pressure levels reduces the dimensions of the open flow paths. Both of these factors increase the patient airway flow resistance. In obstructive lungs the latter may be the dominant mechanism that increases the resistance. Otherwise the former will dominate. With ventilator settings preserving the patient airway resistance, alveolar collapse will not occur and obstructed airways will not constrict excessively.

Gas flow resistance is defined as differences in pressure divided by flow rate. Thus, to measure patient breathing gas flow resistance, alveolar pressure and more proximal pressure are needed, and the flow rate. The more proximal pressure is preferably measured at the trachea at the tip of an endotracheal tube. With tracheal pressure measurement, the effect of endotracheal tube resistance is eliminated from measurement. In certain circumstances, endotracheal tube resistance may be dominant in fading out the changes in patient airway resistance.

The lung is surrounded by the chest. Thus, the alveolar pressure has superimposed thereon the tension forces of the lung tissue and the weight of the chest. At the more proximal pressure, resistive pressure losses are superimposed to this. Thus, when calculating the differences in pressures over patient breathing gas flow resistance, the effect of the chest is subtracted providing specific measurement of the property of the lung alone.

The method of the invention requires alveolar- and proximal pressure determination at different lung pressures or volumes. Patient airway resistance is calculated combining these measurements with flow measurement. Plotting the resistance against the lung pressure or volume gives a within-breath distribution of the resistance. An increase of this resistance at end-expiration volume or pressure indicates lung collapse.

A method to measure volume-specific alveolar pressure is presented in British Journal of Anaesthesia 91 (1):92-105 (2003). This method provides a continuous breath-to-breath alveolar pressure curve using the measured tracheal pressure and breath flow. The breath flow can be measured with a sensor located close to the patient airways, preferably between the endotracheal tube and the Y-piece of the breathing circuit, or alternatively the flow information of the ventilator can be used. The measured flow has to be, however, in synchrony with the measured pressure, which makes the use of the latter more difficult due to varying breathing circuit configurations.

DETAILED DESCRIPTION

Figure 1:
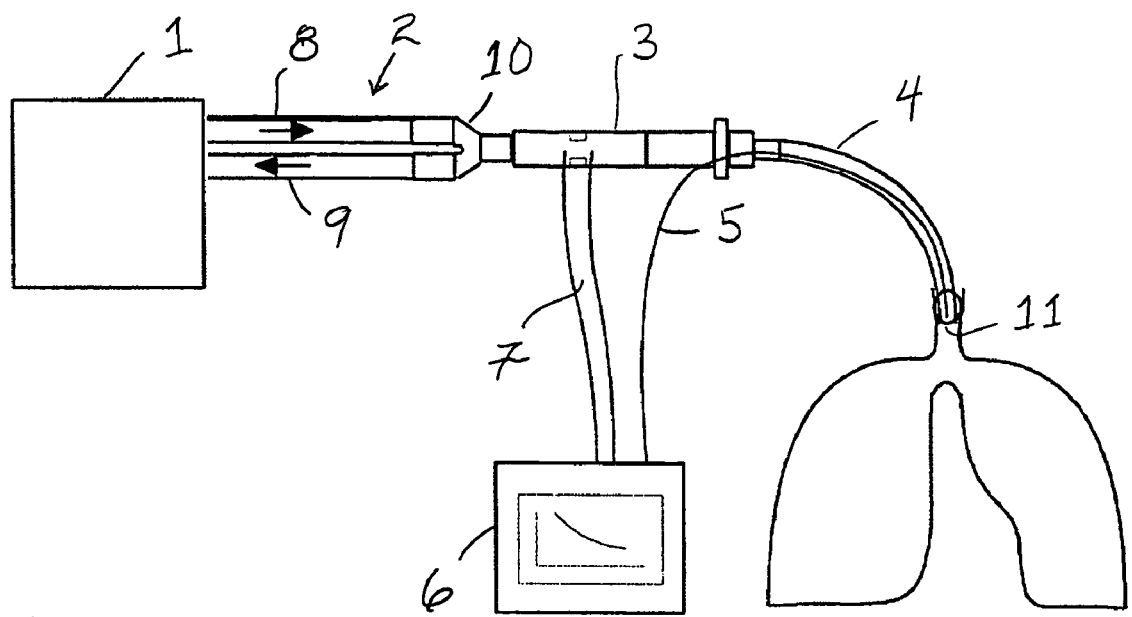
FIG. 1 presents the breathing circuit adopted to monitor the within-breath distribution of patient airway flow resistance.

The invention is applied in connection with artificial breathing. An example setup is presented in FIG. 1. This setup comprises ventilator 1, breathing circuit 2, flow sensor 3, endotracheal tube 4 positioned in patient's trachea, a tracheal pressure sensing system 5, and monitoring equipment 6 receiving the tracheal pressure signal from sensing system 5 and flow sensor signal through flow signal transmission line 7.

The breathing circuit comprises inspiratory 8 and expiratory 9 limbs and Y-piece 10 connecting the limbs together and directing the gas flow to and from the patient. Flow sensor 3 may be any type of sensor sensitive to gas flow direction and magnitude, like thermal mass flow sensor, pitot-tube, pneumotachograph, or ultrasonic flow sensor. The flow signal transmission line 7 is respectively fitted to carry pneumatic or electrical signals.

The tracheal pressure measuring system may be a pneumatic or liquid filled catheter to transmit the pressure signal from the measurement point 11 within the trachea to the pressure sensor located outside the trachea, preferably within the monitoring equipment 6. Alternatively, micro-mechanical pressure sensor may be positioned in a catheter tip and the signal transmitted electrically or optically to the monitor 6.

Alternatively, tracheal pressure can be determined by modelling the pressure drop of the endotracheal tube as a function of tube flow. Guttmann presented such tube modelling in Anesthesiology 79:503-513, 1993. An advantage of such method would be the omission of the tracheal catheter. A disadvantage of such method is that the modelling is valid only for clean tubes, and secretion accumulation is common in intensive care units.

Figure 4:
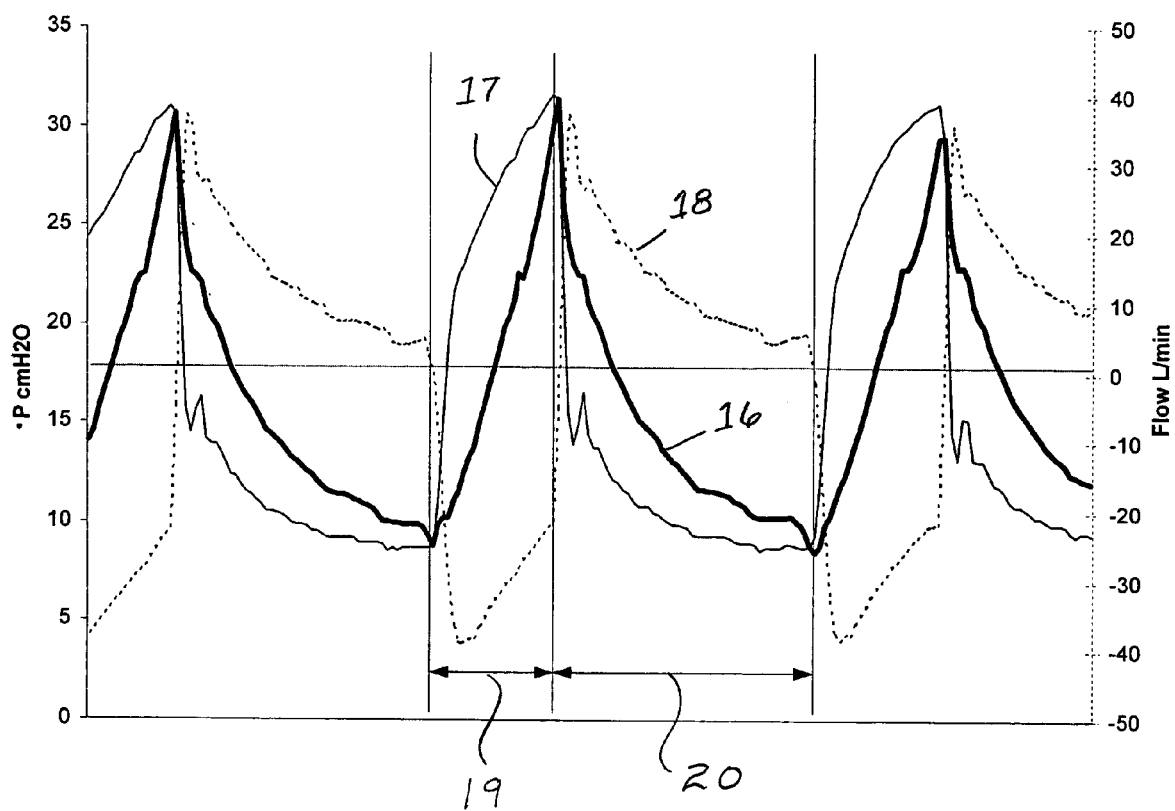
FIG. 4 presents the signals for patient resistance measurement.

Monitor 6 converts the flow and tracheal pressure signals to respective flow and tracheal pressure values using a programmed calibration table. The flow is integrated over time producing the volume information. Alveolar pressure may be calculated from the volume and tracheal pressure signals, as introduced in the British Journal of Anaesthesia 91 (1):92-105 (2003) as dynostatic pressure. The alveolar and tracheal pressures are then referred for coincidence with the flow values. This reference can be achieved for example by plotting both pressure and flow values over time as presented on FIG. 4, which shows alveolar 16 and tracheal 17 pressure curves and flow 18 curve for three breaths. Differences in the alveolar- and tracheal pressures are calculated and divided with the respective flow value giving the resistance.

Resistance values could be calculated both for inspiratory and expiratory phases of the breath. These phases are presented on FIG. 4 with arrow lines 19 and 20, respectively. The expiratory phase is powered only by the elastic forces of the lung and is therefore similar to all artificial ventilation modes. The ventilator powers the inspiration phase against lung elasticity and the flow pattern varies among different ventilation modes. Also, spontaneous breathing may disturb the measurement during inspiration. Therefore the expiration phase is preferred for the resistance measurement.

Patient flow resistance can be estimated also with inspiration flow interrupter technique. During inspiration, measured airway (or tracheal) pressure (Pmax) is a sum of the lung opening and chestwall pressures, and resistive losses of the airways. When the flow is interrupted, the flow-dependent resistive losses disappear and the pressure immediately after the interruption (P1) represents the lung opening and chestwall pressure, ie. alveolar pressure. Subtracting the latter from the former and dividing the difference with flow recorded immediately before the interruption gives the resistance at the lung volume at which the inspiration was interrupted. Using airway pressure to record Pmax and P1 the resistance also includes endotracheal tube resistance. Subtracting tabulated tube specific characteristics gives the patient airway resistance. Using pressure measured from the trachea, tube resistance is excluded. Repeated interruptions at different lung volumes provide a set of volume specific resistance values. Instead of Pmax and P1, Pmax and the end-interruption pressure (Pplat) recorded when the lung and breathing circuit pressures are equilibrated, or P1 and Pplat, can be used for the resistance calculation.

Figure 2:
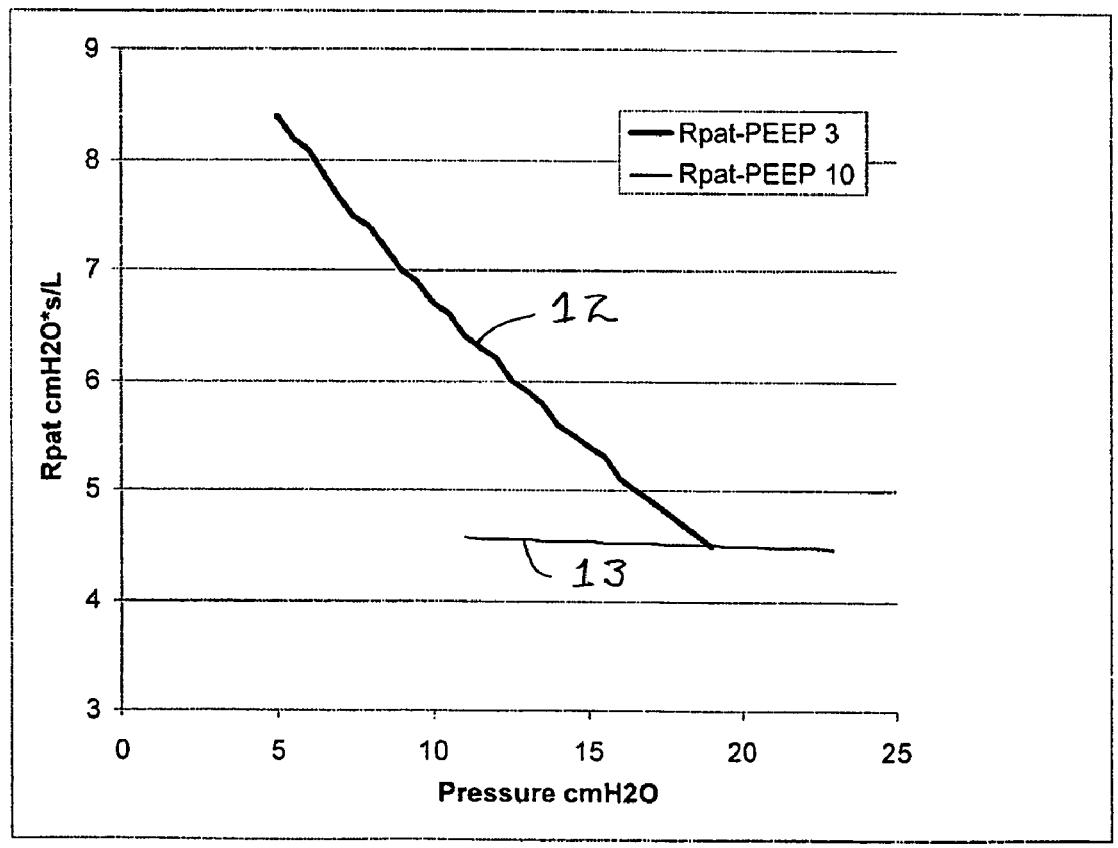
FIG. 2 is an example of within-breath patient flow resistance measured with two different PEEP settings.

FIG. 2 presents the resistance on the ordinate against pressure on the abscissa. This pressure may be alveolar- or tracheal pressure or when plotting the expiration resistance, even airway pressure measured proximal to the endotracheal tube. Two curves with different PEEP values, 3 and 10 cmH2O, represented by numbers 12 and 13 respectively, are presented. Increasing resistance along with pressure decrease towards the end of expiration clearly demonstrates lung collapse at end expiration with PEEP 3. Increasing the PEEP to 10 cmH2O prevents the lung collapse and the resistance is preserved throughout expiration. The absolute value of the expiratory resistance may vary from patient to patient depending upon lung dimensions and structure. The resistance of a non-collapsing lung for a normal adult patient is typically 5 cmH2O/(L/s) or less. In obese or patients having obstructed airways or other lung injury, the non-collapsing resistance may exceed 10 cmH2O/(L/s). It is desirable that resistance remains essentially constant to prevent periodic opening and closing during the breath cycle. This means that the targeted resistance at low lung volume exceeds the high lung volume resistance preferably less than 10%, but at highest less than 30%. The patient values shown in FIG. 2 meet such criterion with PEEP 10.

Figure 3:
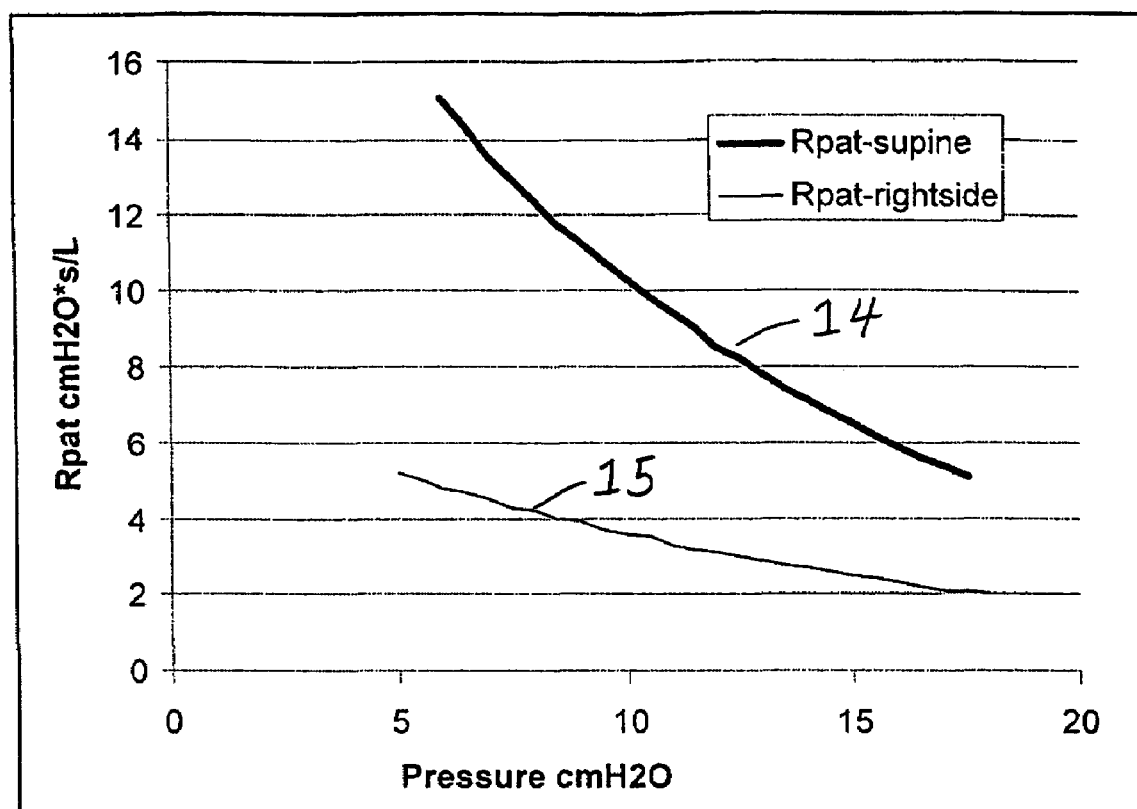
FIG. 3 is an example of within-breath patient flow resistance measured with two different patient positions.

FIG. 3 shows respective results with a single PEEP of 5 cmH2O but with the patient in two different positions, supine and right side, 14 and 15 respectively. The results clearly indicate the superiority of the right side position over the supine position in preventing end expiratory lung collapse, although it is not totally removed, and further recruitment is needed to achieve the resistance stability requirement.

FIGS. 2 and 3 clearly present the use of the method to control the ventilation in order to prevent periodic lung collapse. Similar graphs can also be obtained before and after a recruitment manoeuvre, presuming it was effective.

While a preferred embodiment of the present invention is described and depicted herein, it is recognized that alternative and equivalent structures and method steps recognized by those skilled in the art can be utilized within the scope of the claimed invention.

What is claimed is:

1. A method for monitoring lung collapse, the method comprising the steps of:
   determining, using a tracheal pressure sensing system, proximal pressure during at least two instances in a breathing cycle, one of the instances representing a higher lung volume and the other representing a lower lung volume;
   determining alveolar pressure at the respective instances;
   determining breathing gas flow at the respective instances;
   calculating, using a monitor, alveolar resistance based upon the determined proximal pressures, alveolar pressures and the breathing gas flows;
   plotting a within-breath distribution of alveolar resistance on a graph; and
   assessing a state of lung collapse based upon the calculated alveolar resistance.

2. The method of claim 1, wherein the step of determining the proximal pressure is further defined as determining a tracheal pressure.

3. The method of claim 2, wherein the tracheal pressure is measured at the trachea at a tip of an endotracheal tube.

4. The method of claim 1, further comprising the step of plotting the alveolar resistance against lung pressure on a graph representing within-breath distribution of the resistance.

5. The method of claim 1, further comprising the step of plotting the alveolar resistance against lung volume on a graph representing within-breath distribution of resistance.

6. The method of claim 1, further comprising the step of adjusting at least one ventilatory parameter based on the calculated alveolar resistance.

7. The method of claim 6, further defined as adjusting a PEEP.

8. The method of claim 1, further comprising the step of adjusting a patient position based on the calculated alveolar resistance.

9. The method of claim 1, further comprising the step of performing a recruitment manoeuvre based on the calculated alveolar resistance.

10. The method of claim 1, wherein the tracheal pressure is determined by modelling pressure drop in an endotracheal tube as a function of tube flow.

11. The method of claim 1, wherein alveolar resistance is estimated with an inspiration flow interrupter technique.

12. The method of claim 1, further comprising the step of calculating resistance for both inspiratory and expiratory phases of the breathing cycle.

* * * * *